United States Patent
Lawrence et al.

(10) Patent No.: US 6,239,293 B1
(45) Date of Patent: May 29, 2001

(54) PROCESS FOR PRODUCING DIKEGULAC, ITS SALTS AND DERIVATIVES

(75) Inventors: Lowell J. Lawrence; Stefan Kwiatkowski; Steven G. Mobley, all of Lexington, KY (US)

(73) Assignee: PTRL East, Inc., Richmond, KY (US)

( * ) Notice: Subject to any disclaimer, the term of this patent is extended or adjusted under 35 U.S.C. 154(b) by 0 days.

(21) Appl. No.: 09/511,508

(22) Filed: Feb. 23, 2000

(51) Int. Cl.$^7$ .................................................. C07D 493/14
(52) U.S. Cl. ................................................. 549/361
(58) Field of Search ............................................. 549/361

(56) References Cited

U.S. PATENT DOCUMENTS

| | | |
|---|---|---|
| 2,301,811 | 11/1942 | Reichstein . |
| 3,043,749 | 7/1962 | Huang . |
| 3,234,105 | 2/1966 | Motizuki . |
| 3,832,355 | 8/1974 | Jaffe . |
| 4,007,206 | 2/1977 | Szkrybalo . |
| 4,337,080 | 6/1982 | Szkrybalo . |
| 5,688,971 | 11/1997 | Kwiatkotski . |

Primary Examiner—Ba K. Trinh
(74) Attorney, Agent, or Firm—King and Schickli, PLLC

(57) ABSTRACT

Dikegulac, its salts and related derivatives are prepared by reacting 2-Keto-L-gulonic acid with 2,2 dimethoxypropane at an elevated temperature in the presence of a catalytic amount of a strong acid. This produces a reaction intermediate which is then reacted with a base to complete hydrolysis and produce an acid salt of dikegulac. Simple concentration and phase separation techniques are used to provide a more efficient, environmentally friendly and cost effective process.

12 Claims, No Drawings

PROCESS FOR PRODUCING DIKEGULAC, ITS SALTS AND DERIVATIVES

TECHNICAL FIELD

The present invention relates generally to a process for the preparation of di-O-isopropylidene-2-Keto-L-gulonic acid (dikegulac) as well as its salts and related derivatives (e.g., esters).

BACKGROUND OF THE INVENTION

Dikegulac, its salts, and related derivatives are well known in the art to be useful as plant growth regulators and/or herbicides. Methods for the preparation of dikegulac, its salts, and related derivatives are described in, for example, U.S. Pat. No. 3,832,355 to Jaffe et al; U.S. Pat. No. 4,007,206 to Szkrybalo, U.S. Pat. No. 4,337,080 to Szkrybalo, and U.S. Pat. No. 5,688,971 to Kwiatkowski et al.

The present invention relates to a novel method for the preparation of dikegulac, its salts and related derivatives, from 2-Keto-L-gulonic acid. 2-Keto-L-gulonic acid is an important, well known and readily available intermediate in the manufacture and production of vitamin C. It is derived from sorbitol which is first oxidized to L-sorbose by bacteria. The L-sorbose is then subjected to condensation with acetone in the presence of sulfuric acid followed by oxidation with permanganate and hydrolysis of the diisopropylidene derivative (dikegulac) by boiling in the presence of an acid. This procedure is described in, for example, U.S. Pat. No. 2,301,811 to Reichstein. Also, much more efficient and cost effective processes to directly produce 2-Keto-L-gulonic acid are known. They do not involve its diisopropylidene derivative (dikegulac) as an intermediate. Biochemical oxidation using Pseudomonas is described in U.S. Pat. No. 3,043,749 to Huang while biochemical oxidation using Pseudomonas and Acetobacter is described in U.S. Pat. No. 3,234,105 to Motizuki, et al.

In the prior art, it has also been known to prepare dikegulac, its salts, and related derivatives by the treatment of 2-Keto-L-gulonic acid with 2,2-dimethoxypropane, (see U.S. Pat. No. 5,688,971 to Kwiatkowski et al.). However, the process uses a number of filtration, trituration, and drying steps which increase the time and cost needed to prepare the final product. In addition, the process of the prior art Kwiatkowski et al. patent uses large volumes of solvents. Although the prior art Kwiatkowski et al. process provided an improved approach for the preparation of dikegulac, the process described is still not as cost effective as it could be.

SUMMARY OF THE INVENTION

It is, accordingly, one object of the present invention to provide a new process for producing dikegulac, its salts, and related derivatives using readily available starting materials including 2-Keto-L-gulonic acid, an important and readily available intermediate from the production or manufacture of vitamin C.

A further object of the present invention is to provide a safe and effective process for the efficient and economical production of dikegulac, its salts, and related derivatives, well known to be useful as plant growth regulators and/or herbicides.

It is another object of the present invention to provide a process for the production of dikegulac, its salts, and related derivatives that is less time consuming and more cost efficient than the processes previously known.

Other objects and advantages of the present invention will become apparent as the description thereof proceeds.

In satisfaction of the forgoing objects and advantages there is provided by this invention a process for producing dikegulac. The process comprises reacting 2-Keto-L-gulonic acid

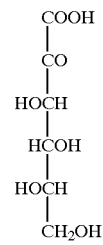

with a reagent selected from a group consisting of 2,2-dimethoxypropane and a mixture of 2,2-dimethoxypropane and acetone in the presence of a catalytic amount of a strong acid (e.g. sulfuric acid, an alkylsulphonic acid, an arylsulphonic acid) at an elevated temperature between 30°–50° C. and still more specifically between 35–45° C. (e.g. approximately 40° C.) to produce a reaction intermediate identified by structural formula (1).

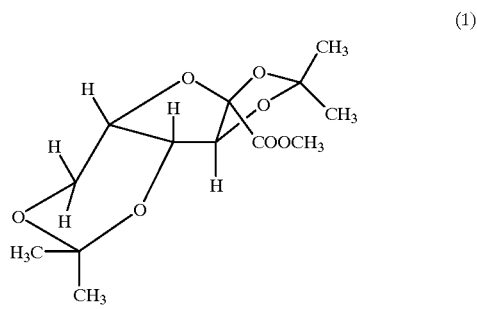

This is followed by the step of reacting the reaction intermediate of formula (1) with a base to complete hydrolysis and produce an acid salt having a chemical formula (2)

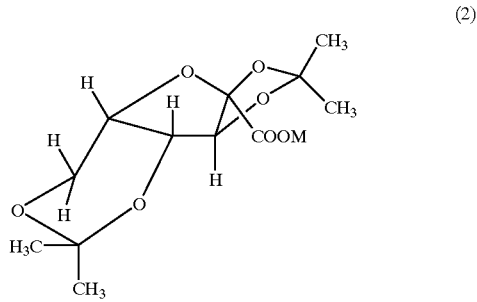

wherein $M^+$=sodium, potassium, ammonium, calcium, magnesium, copper, as well as other members of the alkali and alkaline earth metal groups of the periodic table. The process may further include reacting the acid salt with an acid to produce dikegulac. Preferably, from a stand point of efficiency and cost of production the base utilized in the process is sodium hydroxide and the acid utilized is sulfuric acid.

DETAILED DESCRIPTION OF THE INVENTION

As indicated above, the present invention relates to a new and unique process for producing dikegulac, its salts, and related derivatives. Dikegulac, many of its salts and many of its related derivatives provide post-emergent and/or pre-emergent plant growth regulant activity and herbicidal activity. Some specific applications of plant growth regulation include preventing lodging of cereals; increasing production of harvestable tea leaves by promoting side branching; inhibiting sprouting of potatoes and onions in storage; suppressing growth of grass, trees, shrubs and other vegetation in decorative lawn areas, parks, golf courses, and along highways and other rights of way; accelerating fruit ripening and thus aiding mechanical harvesting by single or reduced number of pickings; defoliating cotton for mechanical harvest; inhibiting new growth of defoliated cotton and, thus, reducing standing of fiber during mechanical harvesting; increasing the quality of the harvested crop, e.g., sugar content of sugar cane, sugar beets, grapefruit, grapes, and other fruits; aiding mechanical harvesting of nut crops by accelerating ripening, stimulating husk cracking and promoting abscission; protecting crops from drought; protecting fruit crops from frost by stimulating early dormancy and/or preventing premature breaking of dormancy; increasing latex flow of rubber; increasing frost resistance of winter cereals; reducing the flowering or bolting of lettuce, sugar beets and tobacco; controlling tobacco suckering; stimulating increased fruit set of soybeans, peanuts, cotton, tomatoes, melons and other fruits and enhancing fruit color and quality; stimulating branching of potted plants (e.g. heather, azalea, chrysanthemum, and geranium); growth retardation in potted plants (e.g. poinsettia, petunia, chrysanthemum, and azaleas); and stimulating branching of young fruit trees, (e.g. apple and pear).

Advantageously, dikegulac, its salts, and related derivatives, are particularly useful for controlling the growth of grasses and weeds as well as undesired plants that become inadvertently mixed in with desired crops.

As is known in the art, uniform distribution of dikegulac, its salts, and related derivatives, in order to control the growth of grasses and weeds may be achieved in a number of ways. The compound may be mixed with agriculturally acceptable adjuvants conventionally used for such applications in order to formulate solutions, emulsions, dispersions, dusts and/or wettable powders Agriculturally acceptable adjuvants as utilized herein include inert carrier materials such as, for example, surface active agents, carriers, sticking agents, stabilizers, fillers, modifiers, diluents, conditioning agents, and the like as well as other active agricultural materials including herbicides, fungicides, insecticides, and other plant growth regulators that complement the activity of the dikegulac compounds by enhancing the compounds activity or useful life.

Liquid formulations for the dikegulac compounds adapted for direct spraying may, for example, be made as aqueous solutions or as solutions in solvent mixtures known for this purpose. Generally, such solutions are buffered (pH 5–7) by the addition of potassium hydrogen phosphate in order to better stabilize the compounds.

Emulsions may be prepared with 25–50% dikegulac compound and surface active agents such as wetting agents, dispersing agents, emulsifying agents, and the like in sufficient quantity to impart the desired characteristics to the formulation.

Wettable powder pre-mixes for the preparation of aqueous solutions may include from approximately 40–60% dikegulac compound and 60–40% surfactant by weight.

Of course, the forms and rate of application of dikegulac, its salts, and derivatives are very well known in the art.

In accordance with an important aspect of the present invention, dikegulac, its salts and related derivatives (e.g. esters) are prepared in a quick, efficient and effective process by reacting 2-Keto-L-gulonic acid with a reagent selected from a group consisting of 2,2-dimethoxypropane and a mixture of 2,2-dimethoxypropane and acetone in the presence of a catalytic amount of a strong acid, such as sulfuric acid or an alkylsulphonic acid or an arylsulphonic acid such as toluene sulphonic acid, at a temperature in the range of from about 30° C. to about 50° C. (and more specifically 35–45° C. or approximately 40° C.) in order to produce a reaction intermediate having the chemical formula (1).

The reaction intermediate (1) is recovered for further processing using relatively simple concentration and phase separation techniques which replace the slower and more complicated filtration and rotary evaporator concentrating operations used in the prior art approach disclosed in U.S. Pat. No. 5,688,971 to Kwiatkowski et al.

In accordance with the new concentration and phase separation techniques, technical grade toluene is added into the reaction mixture and the temperature in the bath is increased (e.g. to 75° C.) to promote concentration of the methanol/acetone mixture. Distillation is continued until the distillate reaches approximately 68° C.

The residue in the flask is then treated with water, stirred for approximately 15 minutes and left for approximately 30 minutes to allow layer separation. Next, the lower water layer is separated and extracted with toluene. The extract is combined with the major portion of the toluene layer from the flask. The water layer containing inorganic salts and by-products is discarded.

Next is the step of reacting the reaction intermediate of formula (1) with a base (sodium hydroxide) to complete hydrolysis and produce an acid salt having the chemical formula (2) where M=sodium.

It should be appreciated, however, that other bases may be utilized and M may also be potassium, ammonium, calcium, magnesium, copper, as well as other members of the alkali and alkaline earth metal groups of the periodic table.

More specifically describing the hydrolysis operation, an equivalent of a base such as sodium hydroxide solution (e.g. prepared by the addition of 200 g of sodium hydroxide into 1 L of DIUF water) is added to the toluene layer in the flask and stirred for approximately 30 minutes. After the sodium hydroxide addition, the pH of the water layer is monitored. It changes from a pH of approximately 12.0 to a pH of approximately 9.5 at which level it remains.

The reaction mixture is then allowed to separate into layers for approximately 15 minutes. The lower, water layer is collected while the upper toluene layer is discarded. The residual toluene is then stripped out of the water layer at 60° C. under water aspirator vacuum for 15 minutes. Dikegulac sodium quantitatively remains in the water solution.

In accordance with the further aspect of the present invention, the acid salt of formula (2) in the dikegulac sodium water solution may be reacted with an acid such as sulfuric acid in order to produce the compound dikegulac. Dikegulac is also useful as a plant growth regulator or herbicide. Dikegulac may also be utilized as an intermediate in the production of related useful derivatives, The following synthesis and examples are presented to further illustrate the invention, but it is not to be considered as limited thereto.

EXAMPLE 1

1. Reaction of 2-Keto-L-Gulonic Acid Starting Material to Produce Reaction Intermediate of Formula (1).

A 1035 g quantity of 90% pure 2-Keto-L-gulonic acid (containing 10% of hydration water (4.8 mole)), 1920 ml of reagent grade acetone, and 2146 ml of reagent grade 2,2-dimethoxypropane (19.65 mole) were charged into a 12 liter four neck reactor equipped with a mechanical stirrer, a thermometer, a reflux condenser protected with a drying tube, and a stopper. The reactor was placed in a water bath set at 40° C. The mixture was stirred and 11.8 ml of 96% sulfuric acid (a catalytic amount) was added over a five minute period. The reactor was maintained with stirring at 40° C. for four hours with occasional addition of 2,2-dimethoxypropane sufficient to keep about 5% excess of the 2,2-dimethoxypropane during the course of the reaction. Three aliquots of 50 ml of 2,2-dimethoxypropane were added, one aliquot at 2 hours, one aliquot added at 2.5 hours, and the final aliquot added 3 hours from the beginning of the reaction. The excess of the 2,2-dimethoxypropane was monitored by gas chromatography.

After the four hours of reaction time, 72 g of powdered sodium bicarbonate was added to the reactor and the reflux condenser on the reactor was replaced with a Vigreux column equipped with a distillation head. 1920 ml of industrial grade toluene was added to the reactor and the temperature of the water bath was increased to 75° C. A methanol/acetone mixture was distilled off (about 3.8 liters of distillate) until the temperature of the distillate reached 68° C. Then, the residue in the reactor was treated with 1.9 liter of deionized ultrafiltered water. The residue was stirred vigorously for 15 minutes and then allowed to stand for 30 minutes to separate into two layers. The lower, water layer was separated and extracted with 200 ml of toluene. The extract was added to the major portion of the toluene layer from the reactor and the water layer was discarded. The only component in the toluene layer was the dikegulac methyl ester, the intermediate compound of formula (1).

2. The Hydrolysis of the Compound of Formula (1) to Give the Compound of Formula (2), wherein M=Sodium.

The toluene layer and toluene extract of the water layer from above were combined in the reactor and treated with 735 ml of a sodium hydroxide solution (prepared by the addition of 200 g of sodium hydroxide in 1 liter of deionized ultrafiltered water) and stirred vigorously for 30 minutes with the pH of the reaction mixture going from about 8.5 before addition of the sodium hydroxide to about 10.5 after addition of the sodium hydroxide. The reaction mixture was allowed to stand for 15 minutes to separate into two layers. The water layer was collected while the toluene layer was discarded. The residue of any toluene was stripped from the water layer by use of a water aspirator vacuum with the water held at 60° C. for 15 minutes. An amount of 1523 ml of the dikegulac sodium water solution was collected which contained 1023 g of the desired sodium dikegulac, the compound of formula (2), wherein M=sodium, a yield of 72%. The sodium dikegulac had a purity of greater than 96% by $^1$H NMR.

3. The Formation of a Solid Dikegulac Sodium Monohydrate

A 100 ml portion of the dikegulac sodium water solution from above was transferred to a 500 ml rotoevaporator flask and the water was removed by rotoevaporation at 50° C. under water aspirator vacuum. A glassy residue was dried under high vacuum at room temperature to give 67.2 g of a creamy powder of the solid dikegulac sodium, the compound of formula (2), wherein M=sodium.

4. The Formation of a Solid Dikegulac Acid.

A 100 ml portion of the dikegulac sodium water solution from above was placed in a 250 ml round-bottom flask equipped with a mechanical stirrer, a thermometer, and a dropping funnel. The round-bottom flask was placed in an ice-water bath and the reaction solution is stirred vigorously. When the reaction solution reached about 5° C., a 100 ml portion of pre-cooled (5° C.) 2N sulfuric acid is placed in the dropping funnel and added to the reaction solution to maintain the reaction solution temperature below 10° C. and until the pH of the reaction solution reached 2.5. A white solid dikegulac acid precipitated out and was filtered out of the reaction solution. The filtrate was discarded and the precipitate was washed with three 20 ml portions of icy water. The precipitate was air dried to give 62.6 g of the dikegulac acid (of greater than 99% purity, by $^1$H NMR) with a 95% yield.

EXAMPLE 2

The process as set forth in Example 1 is performed with pure 2,2-dimethoxypropane substituted for the mixture of 2,2-dimethoxypropane and acetone in step 1.

EXAMPLES 3–7

The process as set forth in Example 1 is performed with potassium hydroxide, calcium hydroxide, magnesium hydroxide, cupric hydroxide or ammonia water substituted for sodium hydroxide.

The invention has been described herein with reference to certain preferred reagents and starting materials. It should be appreciated, however, that as obvious variations thereon become apparent to those skilled in the art, the invention is not to be considered as limited thereto.

In summary, numerous benefits result from the improved method of the present invention. By increasing the reaction temperature from room temperature to 30–50° C. and using a catalytic amount of strong acid (e.g. sulfuric acid), reaction intermediate (1) is produced quickly and more efficiently. Additionally, much simpler distillation and phase separation techniques are utilized in place of the more complicated filtration, trituration and drying operations of the prior art procedure set forth in U.S. Pat. No. 5,688,971 to Kwiatkowski et al.

Many benefits are derived as a result of these improvements. The new approach is simplified and more technological with a total yield of dikegulac sodium of 72% instead of 46.37%. Almost ten times smaller volumes of solvents, sulfuric acid and sodium carbonate are used in comparison to the prior art process. The total volume of waste products resulting from the new process in comparison to the old process is reduced by a factor of ten. Thus, the present procedure is not only simpler, but also less time consuming and more environmentally friendly while advantageously providing equal quality product with much improved yield. The new process is also approximately three times more cost effective.

What is claimed is:

1. A process for producing dikegulac comprising:

reacting 2-Keto-L-gulonic acid with 2,2-dimethoxypropane at an elevated temperature above 30° C. in the presence of a catalytic amount of an acid catalyst to produce a reaction intermediate having the chemical formula

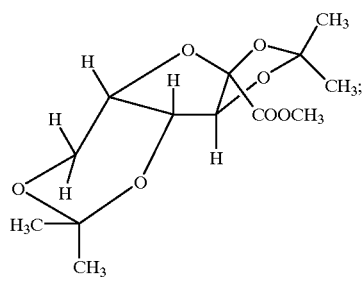

(1)

and reacting said reaction intermediate (1) with a base to complete hydrolysis and produce an acid salt having a chemical formula

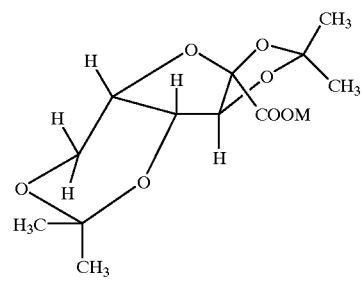

(2)

wherein M⁺=an alkali or alkaline earth metal of the periodic table.

2. The process of claim 1 further including reacting said acid salt with an acid to produce dikegulac acid.

3. The process of claim 2 wherein said base is sodium hydroxide and said acid is selected from a group consisting of sulfuric acid, an arylsulphonic acid and an alkylsulphonic acid.

4. The process of claim 1 wherein said acid catalyst is sulfuric acid or toluene sulphonic acid.

5. A process for producing dikegulac comprising:

reacting 2-Keto-L-gulonic acid with 2,2-dimethoxypropane at an elevated temperature between 30–50° C. in the presence of a catalytic amount of a strong acid to produce a reaction intermediate having the chemical formula

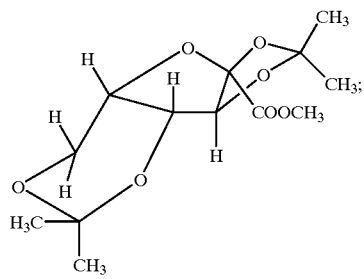

(1)

and reacting said reaction intermediate (1) with sodium hydroxide to complete hydrolysis and produce an acid salt having a chemical formula

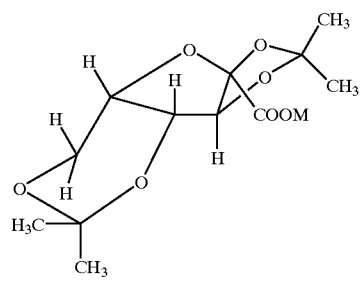

(2)

wherein M=sodium.

6. The process of claim 5, further including recovering reaction intermediate (1) by means of reaction solution concentration, phase separation and collecting a toluene layer with reaction intermediate (1) and discarding a water layer including inorganic salts and reaction by-products.

7. A process for producing dikegulac comprising:

reacting 2-Keto-L-gulonic acid with 2,2-dimethoxypropane at an elevated temperature above 30° C. in the presence of a catalytic amount of an acid catalyst to produce a reaction intermediate having the chemical formula

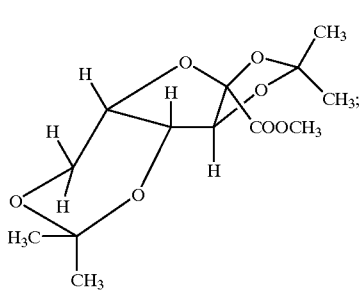

(1)

recovering reaction intermediate (1) by means of reaction solution concentration and phase separation; and reacting said reaction intermediate (1) with a base to complete hydrolysis and produce an acid salt having a chemical formula

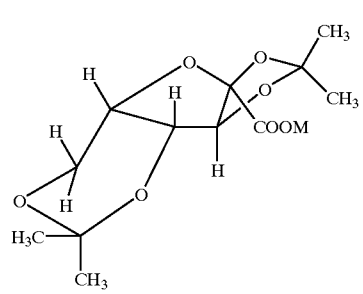

(2)

wherein M⁺=an alkali or alkaline earth metal of the periodic table.

8. A process for producing dikegulac comprising:

reacting 2-Keto-L-gulonic acid with 2,2-dimethoxypropane at an elevated temperature above 30° C. in the presence of a catalytic amount of an acid catalyst to produce a reaction mixture including a reaction intermediate having the chemical formula

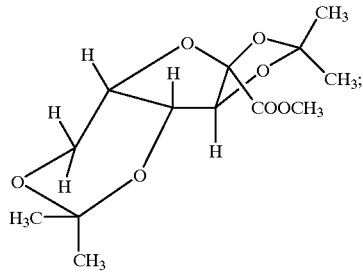
(1)

distilling said reaction mixture;

recovering said reaction intermediate from said reaction mixture; and reacting said reaction intermediate (1) with a base to complete hydrolysis and produce an acid salt having a chemical formula

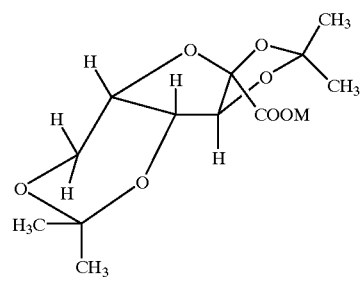
(2)

wherein $M^+$=an alkali or alkaline earth metal of the periodic table.

9. The process of claim 8, including adding toluene to said reaction mixture prior to distilling.

10. The process of claim 9, including removing inorganic salts and by-products following distillation by treating with water.

11. The process of claim 9, including collecting a toluene layer including said reaction intermediate following distilling.

12. The process of claim 11, including collecting a water layer including said acid salt following reacting said reaction intermediate with said base.

* * * * *